US008528137B2

(12) United States Patent
Johnson et al.

(10) Patent No.: US 8,528,137 B2
(45) Date of Patent: Sep. 10, 2013

(54) COLLAPSIBLE LITTER WITH INTEGRATED EQUIPMENT BAG

(75) Inventors: Ross Johnson, Anderson, SC (US); Alan Hester, Greenville, SC (US); Erick Ward, Anderson, SC (US); Chris Kopp, Edmonton (CA)

(73) Assignee: Tactical Medical Solutions, Inc., Anderson, SC (US)

( * ) Notice: Subject to any disclaimer, the term of this patent is extended or adjusted under 35 U.S.C. 154(b) by 0 days.

(21) Appl. No.: 12/775,087

(22) Filed: May 6, 2010

(65) Prior Publication Data

US 2011/0271450 A1 Nov. 10, 2011

(51) Int. Cl.
*A61F 5/37* (2006.01)

(52) U.S. Cl.
USPC ............................ 5/628; 5/625; 5/626; 5/627

(58) Field of Classification Search
USPC ....................................................... 5/625–628
See application file for complete search history.

(56) References Cited

U.S. PATENT DOCUMENTS

| | | | | | |
|---|---|---|---|---|---|
| 3,110,912 | A | * | 11/1963 | Propst | 5/628 |
| 4,679,260 | A | | 7/1987 | Frettem | |
| 4,970,739 | A | * | 11/1990 | Bradford | 5/625 |
| 5,050,254 | A | * | 9/1991 | Murphy | 5/625 |
| 5,150,487 | A | * | 9/1992 | Hemphill | 5/625 |
| 5,720,303 | A | * | 2/1998 | Richardson | 128/870 |
| 5,978,989 | A | | 11/1999 | Chavez | |
| 6,128,796 | A | | 10/2000 | McCormick et al. | |
| 6,477,728 | B1 | * | 11/2002 | Faz | 5/625 |
| 6,772,764 | B2 | * | 8/2004 | Chapman | 128/870 |
| 7,607,184 | B1 | | 10/2009 | Goodner | |
| 7,774,877 | B2 | * | 8/2010 | Kenalty et al. | 5/626 |
| 7,774,878 | B1 | | 8/2010 | Florea | |
| 2003/0066134 | A1 | * | 4/2003 | Chapman | 5/628 |
| 2005/0172406 | A1 | * | 8/2005 | Post | 5/626 |
| 2007/0136950 | A1 | * | 6/2007 | Zuercher | 5/627 |
| 2009/0038076 | A1 | | 2/2009 | Giduck | |
| 2009/0288255 | A1 | * | 11/2009 | Sakurai et al. | 5/625 |
| 2010/0005593 | A1 | * | 1/2010 | Bowling et al. | 5/627 |

* cited by examiner

*Primary Examiner* — William Kelleher
(74) *Attorney, Agent, or Firm* — Cahn & Samuels, LLP

(57) ABSTRACT

A collapsible litter including a first flexible and elongated body support member having a top surface, a bottom surface, and a plurality of flexible grab strap elements attached to the bottom surface of the body support member. The strap elements extend substantially beyond the surface of the body support member. A second flexible body support member, is disposed on the top of the first flexible elongated body support member, and covers a substantial portion of the first flexible elongated body support member. At least one edge of the second flexible body support member is affixed the top surface of the first flexible body support member forming a compartment with an opening for securing and transporting items such that the first and second body support members form a compartment for securing and transporting items.

4 Claims, 4 Drawing Sheets

COLLAPSIBLE LITTER WITH INTEGRATED EQUIPMENT BAG

I. FIELD OF THE INVENTION

This invention relates in general to the field of stretchers and litters and in particular to the field of collapsible litters.

II. BACKGROUND OF THE INVENTION

Traditionally, portable litters/stretchers are constructed for durability, rigidity and containment of the patient. These characteristics allow the litter to be used in environments such as lifting an individual by wench or airlift, for example, a hiker after a mountain climbing fall, a homeowner from a flooded neighborhood, or a soldier from the battlefield. However, these same characteristics also cause the litter to be bulky and weighty, and can also cause delays in lifesaving extraction.

Traditional portable stretchers are made of heavy-duty material to protect the injured person from contact with the ground and other objects during extraction. Heavier, thicker, and wider construction of the litter base keeps the individual from bruising or sustaining additional minor injuries from terrain over which he or she might be dragged. The use of heavier materials also keeps the patient rigid, better supported, and provides a certain amount of splinting. However, the weight and bulk of typical portable stretchers can be a burden to a soldier or first responder carrying the litter on their person.

Some portable stretchers have side and bottom flaps which extend from the base. While useful for some applications, the flaps take time to engage, and they can interfere with speedy extraction and medical treatment. For example, foot flaps are unnecessary in most manual-lifting circumstances in which a drag litter is used. However, most roll-up litters/stretchers are provided with foot flaps regardless of whether they are designed for airlifting thereby adding additional bulk and weight to the litter.

Some stretchers use heavy and complicated equipment. For example, a half-body stretcher provides protection only to the top half of the individual and requires an additional half-body stretcher to secure the lower half of the patient's body. The second half-body stretcher must be carried on the back of a second soldier or first responder, causing delays in deployment and possible deficiency if a second half-body stretcher is not available. Some stretchers use large durable buckles or wide heavy straps to retain the patient. The large bulk and weight of traditional portable stretchers/litters sometimes require separate bags for storage and transport.

While these devices might be useful in some scenarios to securely encase a patient prior to, for example, vertical movement (airlift), they add weight and bulk to the stretcher, making it harder to carry on backpacks in a mobile military unit. Weight and bulk are not desirable characteristics in certain circumstances. For example, army soldiers and frontline medics are generally more intent on quick extraction than keeping a wounded soldier fully splinted or protected from minor bruises and cuts. Traditional devices require time to deploy to provide vertical movement to a casualty. Time is an expensive luxury for those engaged in an emergency situation.

Some stretchers have been designed to compact into a cylindrical roll for storage and transportation. This configuration allows soldiers to carry the litter, on a backpack for example. However, common designs of the roll-up stretcher are typically relatively heavy and bulky. These roll-up litters are also wide in dimension, 2 feet (24 inches) or more, and as long as eight (8) feet in length, some having additional length to create a flap for covering the patient's feet.

While larger dimensions and heavier materials typically add strength to a stretcher device, the unnecessary weight and bulk tends to complicate packaging and makes seamless integration into existing combat or safety equipment unlikely. This bulk becomes a significant problem since a major consideration for packaging and fielding collapsible litter designs is to afford a broader distribution of evacuation platforms. Ideally, each operator in a theatre of action would carry at least one litter that can quickly be deployed to assist in a casualty's evacuation, or to assist in his or her own evacuation if injured.

A somewhat recent attempt to address the problems associated with the broad distributing portable litter devices where among combatants or first responders has been to incorporate the litter device into an article of clothing, for example a vest or a waist pack. This approach typically requires the litter to be attached to the article of clothing as in U.S. Pat. No. 7,607,184. A significant drawback of this approach is that a new article of clothing, for example a vest incorporating the litter device necessarily replaces existing vests. This is expensive and necessarily inefficient, particularly in a military context since logistically, a quartermaster or equipment supplier must collect the previously issued vests and issue a new ones. The old articles of clothing are modified or discarded, making this approach expensive, complicated and generally inefficient to employ. In addition since the litter is attached to an article of clothing, the litter can only be used to evacuate the individual who happens to be wearing the article of clothing.

Another approach suggested by U.S. Pat. No. 7,607,184 is to use a waist pack with the litter attached thereto from which the litter is deployed. However, the waist pack approach also requires the issuance of a new and independent piece of equipment that must be worn around the operator, soldier or first responder and/or the casualty's waist for deployment. First, if the casualty doesn't happen to be wearing the waist pack, the waist pack must be removed from the wearer's waist and placed on the casualty's waist before the litter is deployed. Secondly, adding another piece of equipment to a user's waist, in addition to the existing equipment, weapons, canteen, ammunition, radio, ALICE pack, hoist, harnesses, MOLLE-system or other existing modular system or equipment carried by an operator, soldier or first responder is also problematic. Due to the added bulk and restrictive placement on the waist, incorporation of such a system with existing equipment is cumbersome at best. Conceivably, a first responder may have to pick and choose what equipment he can carry on his waist, based on mobility, space, mission and packaging requirements.

There also exists a need for an easily carried and easily deployed duffel bag to store and/or transport equipment. For example, in view of the non-linear warfare and often sensitive equipment carried by an operator or soldier, it is often necessary to carry the casualty's equipment with him. Also insurgents use discarded equipment as booby trap enticements or for other purposes. In the case of head trauma or injury, access to the casualty's head gear or helmet, can provide a doctor or other care giver a quick means to evaluate the type of trauma the evacuee\casualty likely suffered. In the past, a duffel bag or equipment bag has been a separate piece of equipment. Typically, this type of equipment is not carried by an operator, combatant or first responder and certainly is not carried by a casualty. Thus an easily accessible bag or container to secure, transport or store a wounded solder's equipment and keep that equipment with him during his evacuation is also needed.

III. SUMMARY OF THE INVENTION

Notwithstanding the usefulness of the above-described structures, a need still exists for a strong, lightweight, convenient, flexible and easily deployable portable litter system that can be seamlessly integrated into existing combat or rescue equipment such as the MOLLE-system, incorporating a duffel bag with the ability to store or secure the casualty's equipment when he is evacuated from the action zone or moved to a rigid stretcher.

Accordingly disclosed is a collapsible litter that is strong, lightweight, convenient, flexible and easily deployable, and designed to be seamlessly integrated into existing and future tactical and rescue equipment, incorporating a duffel bag to store and transport equipment.

To this end, the disclosed collapsible litter features a structure including a first flexible and elongated body support member having a top surface, a bottom surface, and a plurality of flexible grab strap elements attached to the bottom surface of the body support member. The strap elements extend substantially beyond the surface of the body support member. A second flexible body support member, is disposed on the top of the first flexible elongated body support member, and covers a significant portion of the first flexible elongated body support member. At least one edge of the second flexible body support member is affixed the top surface of the first flexible body support member forming a compartment with an opening for securing and transporting items. At least one flexible anchor/body strap element is included. The flexible body strap element is attached to and extends across the surface of the first flexible elongated body support member. At least one of the flexible body straps is disposed proximate to the compartment opening and the end of the body strap extends substantially beyond the body support member and has an attachment means disposed thereon.

Also disclosed is a collapsible litter including a first flexible and elongated body support member, constructed of a synthetic fabric, having a top surface and a bottom surface and a plurality of flexible grab strap elements attached to the bottom surface of the body support member. The strap elements extend substantially beyond the surface of the body support member and the edge of each extended end of the grab strap elements is also attached to a surface of the elongated body support member forming a loop grab handle.

The collapsible litter also includes a second flexible body support member constructed of a synthetic fabric, disposed on the top of the first flexible elongated body support member. At least one edge of the second flexible body support member is affixed to the top surface of the first flexible body support member forming a compartment for securing and transporting items or equipment. The unsecured edge of the second flexible body support member preferably has an apparatus to secure the compartment.

The litter also includes at least one flexible body strap element, the body strap element being attached to and extending across the bottom surface of the first flexible elongated body support member, at least one end of the body strap extends substantially beyond the body support member and has an attachment means disposed thereon. At least one body strap is disposed proximate to the compartment opening.

Also disclosed is a system for casualty evacuation including a compact collapsible litter having a first flexible and elongated body support member having a top surface and a bottom surface and a plurality of flexible grab strap elements attached to the bottom surface of the body support member, the strap elements extending substantially beyond the surface of the body support member and a second flexible body support member, the second body support member being disposed on the top of the first flexible elongated body support member, at least one edge of the second flexible body support member is affixed to the top surface of the first flexible body support member. The first and second body support members form a compartment having an opening for securing and transporting items or equipment.

The litter also includes at least one flexible body strap element. Preferably, the body strap element is attached to and extends across the bottom surface of the first flexible elongated body support member. At least one end of the body strap element preferably extends substantially beyond the body support member and has an attachment means disposed thereon.

The system also includes a storage device for the compact collapsible litter, the storage device having a sealable compartment for housing the litter. The storage device also includes an attachment apparatus for attaching and integrating the storage device to existing equipment carried by a potential casualty or care giver.

As used herein "connected" includes physical, whether direct or indirect, permanently affixed or adjustably mounted. Thus, unless specified, "connected" is intended to embrace any operationally functional connection.

As used herein "substantially," "generally," "proximate," and other words of degree are relative modifiers intended to indicate permissible variation from the characteristic so modified. It is not intended to be limited to the absolute value or characteristic which it modifies but rather possessing more of the physical or functional characteristic than its opposite, and preferably, approaching or approximating such a physical or functional characteristic.

In the following description, reference is made to the accompanying drawing which is shown by way of illustration to the specific embodiments in which the invention may be practiced. The following illustrated embodiments are described in sufficient detail to enable those skilled in the art to practice the invention. It is to be understood that other embodiments may be utilized and that structural changes based on presently known structural and/or functional equivalents may be made without departing from the scope of the invention.

IV. BRIEF DESCRIPTION OF THE DRAWINGS

In order to describe the manner in which the invention can be obtained, a more particular description of the invention briefly described above will be rendered by reference to specific embodiments thereof which are illustrated in the appended drawings. Understanding that these drawings depict only typical, exemplarily embodiments of the invention and are not therefore to be considered to be limiting of its scope, the invention will be described and explained with additional specificity and detail through the use of the accompanying drawings.

V. DETAILED DESCRIPTION

Figure 1:
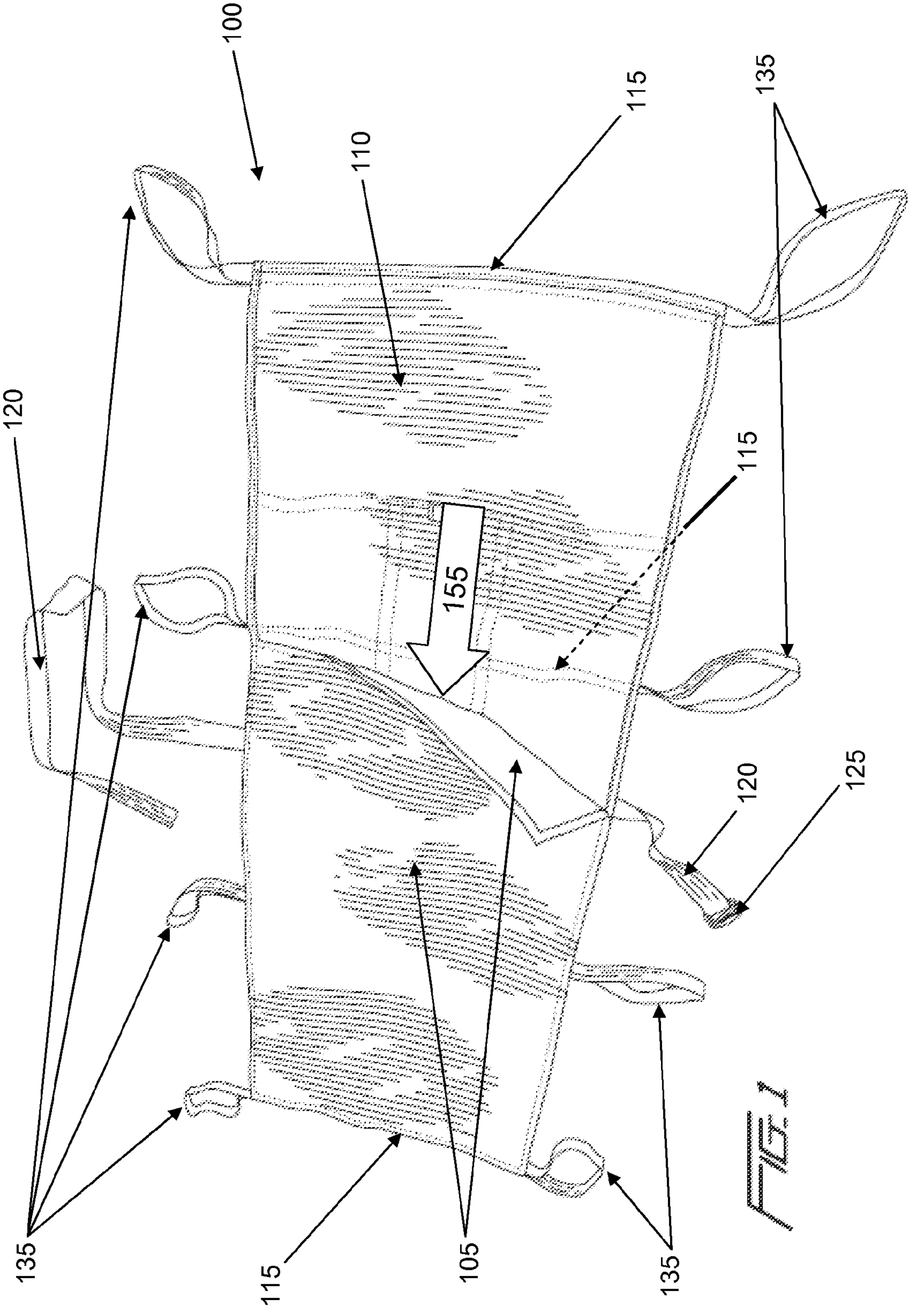
FIG. 1 illustrates a top view of an exemplarily embodiment of the collapsible litter apparatus
Figure 2:
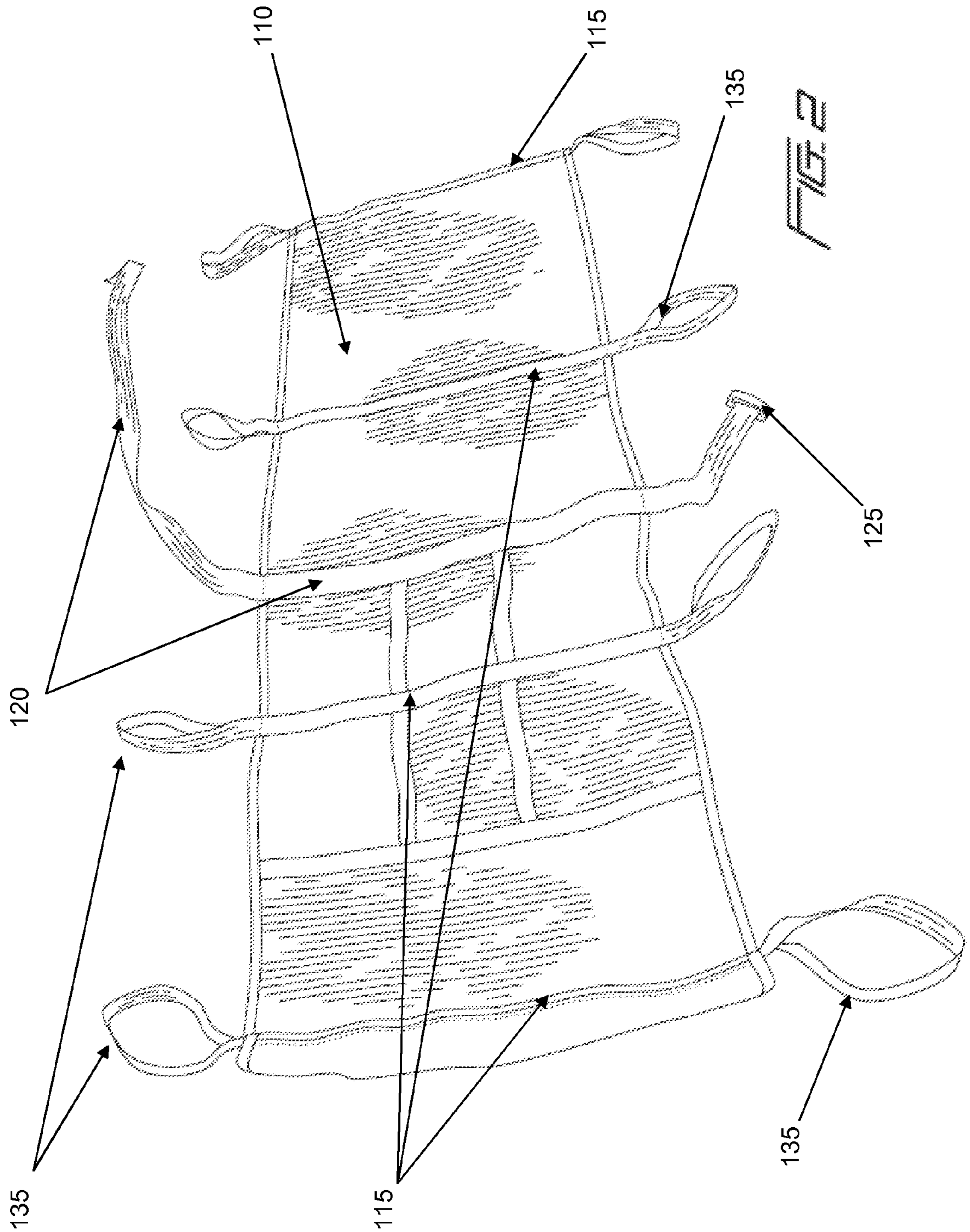
FIG. 2 illustrates a bottom view of an exemplarily embodiment of the collapsible litter apparatus of FIG. 1.

Referring now to the figures wherein like reference number numbers denote like elements, FIG. 1 shows a top view of an exemplarily embodiment of the collapsible litter apparatus 100. FIG. 2 shows the bottom view of the exemplarily embodiment of the litter shown in FIG. 1.

The collapsible litter apparatus incorporates several features designed to facilitate dual use as a litter, and as a duffel bag to carry, store or otherwise secure items. The litter apparatus includes a plurality of flexible body support members. The flexible body support members are affixed to each other to create a reinforced structure defining a surface on which a casualty may be placed for triage and evacuation.

The litter apparatus also features a plurality of flexible grab strap elements attached to the reinforced surface defined by the body support members that function as carry handles to facilitate easy handling when the litter is loaded with a casualty. These flexible grab strap elements may also be disposed to extend across the bottom of the reinforced surface to further reinforce the casualty receiving surface defined by the flexible body support members. In addition the litter also features one or more body strap elements adapted to secure a casualty to the litter apparatus for efficient transport.

The litter apparatus also features a compartment formed by the attached flexible body support members, accessible through an opening formed where the body support members are not affixed. The compartment facilitates the dual use of the litter apparatus as a litter or as a duffel bag to store and secure equipment or other items. At least one of the body support members is located proximate to the compartment opening, and has a second function serving as a drawstring to cinch the compartment opening to secure items when the litter is used in a duffel bag mode. The body support member also serves as a carry strap when used in the duffel bag mode. The litter apparatus is preferably constructed of strong, flexible and lightweight materials. The litter may be constructed of ballistic materials for enhanced strength, or for use as a supplemental shelter from shrapnel or other projectiles when used in a combat environment.

Referring to FIG. 1 and FIG. 2, the illustrated embodiment includes a collapsible litter 100 having a first flexible and elongated body support member 110 with a top surface and a bottom surface. The body support member 110 features a plurality of flexible grab strap elements 115 attached to the bottom surface of said body support member 110. In the embodiment shown the strap elements 115 extend across and substantially beyond the surface of said body support member 110 and reinforce the body support member. Typically the first flexible and elongated body support member 110 is constructed of a synthetic fabric, however the elongated body support member may be constructed of any lightweight, flexible material, including vinyl, nylon, puncture resistant ballistic materials including Kevlar®, or any other synthetic or natural fabric materials. The litter 100 also has a second flexible body support member 105. The second body support member 105 is disposed on said top of the first flexible elongated body support member 110.

In the embodiment shown, the second flexible body support member 105 has an upper edge region, a lower edge region and a plurality of side edge regions. The second flexible body support member 105 is affixed to the top surface of said first elongated body support member 110 at the lower and side edge regions. The three edge regions of the second flexible body support member 105 are rigidly affixed to the top surface of the first flexible body support member 110 defining the duffel bag compartment.

The edge/s of the second flexible body support member 105 may be affixed to the top surface of the first flexible body support member 110 by sewing the members together, molding the members together during manufacture, riveting the surfaces or attachment via Velcro or other known methods of attachment. When sewn, the seams may feature double or triple stitching, or combinations of stitching, bonding, riveting or Velcro to improve the strength of the litter and the carrying capacity of the duffel bag. The second flexible body support may be constructed of puncture resistant ballistic materials as well.

Figure 3:
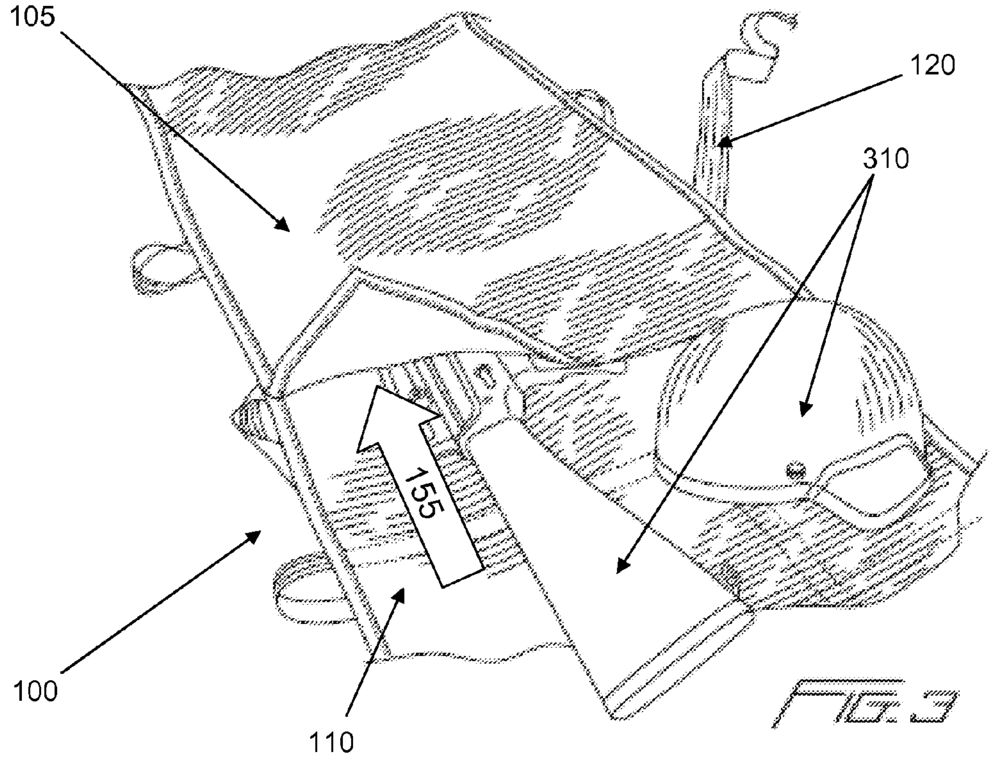
FIG. 3 illustrates a top view of an exemplarily embodiment of the collapsible litter apparatus with the equipment bag in use.

Referring now to FIG. 3, which shows a top view of an exemplarily embodiment of the collapsible litter apparatus 100 with the equipment bag 155 in use and with continued reference to FIG. 1 and FIG. 2, the first 110 and second 105 body support members form a compartment 155 for securing and transporting items or equipment. The edge of each extended end of said grab strap elements 115 is also attached to a surface of the elongated body support member 110 forming a loop grab handle 135.

In at least one embodiment the second flexible body support member is affixed to the first elongated body support member 105 and covers a significant portion of the area defined by the first elongated body support member 110. Typically the second flexible body support member 105 covers 50% or more of the area defined by the first elongate body support member 110. In other embodiments the elongated body support member 110 is substantially covered by the second flexible body support member 105 and defines a compartment having a volume of at least 12 liters.

The shape of the second flexible body support member 105 may vary and it may have rounded edges, straight edges or a combination thereof. Preferably, the second flexible body support member 105 is largely rectangular and has three edges attached to the first elongated body support member 110 to form the compartment. An edge of the second flexible body support member 105 may be attached to the first elongated body support member 110 via a Velcro strip. An edge of the second body support 105 may employ Velcro to allow easy access to and sealing of the compartment. In other embodiments the body support members 105, 110 may have a plurality of cooperating Velcro strips disposed on the engaging body support surfaces to define more than one compartment as well as compartments of varying shapes.

The litter 100 also includes at least one flexible body strap element 120 being attached to and extending across the bottom surface of the first flexible elongated body support member 110. Each end of the body strap 120 extends substantially beyond said body support member 110 and preferably has an attachment means 125 disposed thereon 125. The attachment means may be Velcro®, a buckle assembly, a knot, an adjustable hook and loop or other means. While the litter 100 may employ a plurality of flexibly body strap elements, at least one of the body straps 120 is disposed sufficiently proximate to the compartment opening 155 so as to be used as a drawstring to secure the duffel bag compartment 155. Body strap 120 an is also useful as a handle or carry strap for the litter when configured for use as a duffel bag.

Figure 5:
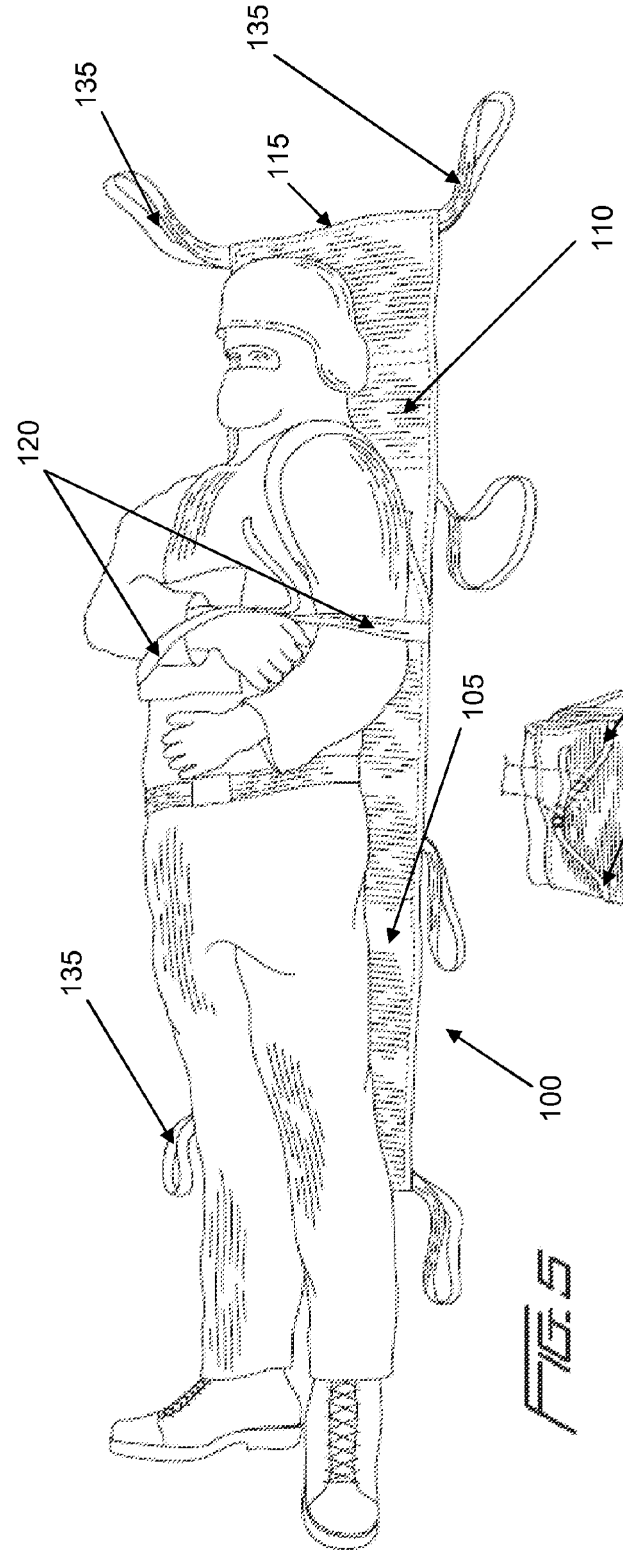
FIG. 5 illustrates an exemplarily embodiment of the collapsible litter apparatus in use as a litter.

FIG. 5 illustrates an exemplarily embodiment of the collapsible litter apparatus 100 when employed in the litter configuration. As shown in the figure, the casualty's body core is positioned upon the litter and a flexible body strap 120 is run across the casualty's waist or chest and cinched or tightened with an attachment means (not shown) to secure the casualty to the litter 100.

As shown in the exemplary embodiment of FIG. 5 the first flexible elongated body support member 110 coupled with the second elongated body support member 105 supports the casualty's body. The loop grab handles 135 facilitate quick and easy transport of the casualty out of area. The double layer structure provided by the dual flexible body support members 105, 110 provides mutual reinforcement facilitating a strong and robust litter, combined with light weight and ease of packaging.

In another embodiment the unsecured edge of said second flexible body support member incorporates an attachment apparatus to seal the compartment. The attachment apparatus may be a Velcro® mechanism, snaps, a zipper or other attachment means known in the art.

In another embodiment the litter incorporates a structure optimized to allow dual use; the use of the equipment compartment of the litter for storage while the litter is being used to evacuate a casualty. In this embodiment the second body support member is disposed on a surface opposite the casualty carrying surface and an unsecured edge of said second flexible body support member incorporates a second, independent attachment apparatus to secure and/or seal the compartment, for example snaps, a zipper or Velcro® strip.

In this embodiment the secured edges of the second flexible body support member feature a reinforced structure with reinforced stitching to strengthen the litter and particularly the equipment compartment. The grab loops 135 also include reinforced stitching at the junction of the loop and the common edges of the first elongated body support member 110, the second body support member 105 and the grab loop 135.

In operation the equipment bag is disposed on the underside, exposing the equipment bag for use, even when a casualty is physically on the litter. Excess or necessary equipment, is placed in the compartment and the casualty is placed on the elongated body support member 110 which is oriented to face up. The equipment bag, on the underside, is sealed with the Velcro strip and the casualty is removed from the area, with his equipment contained in the bag on the underside of the litter.

Figure 6:
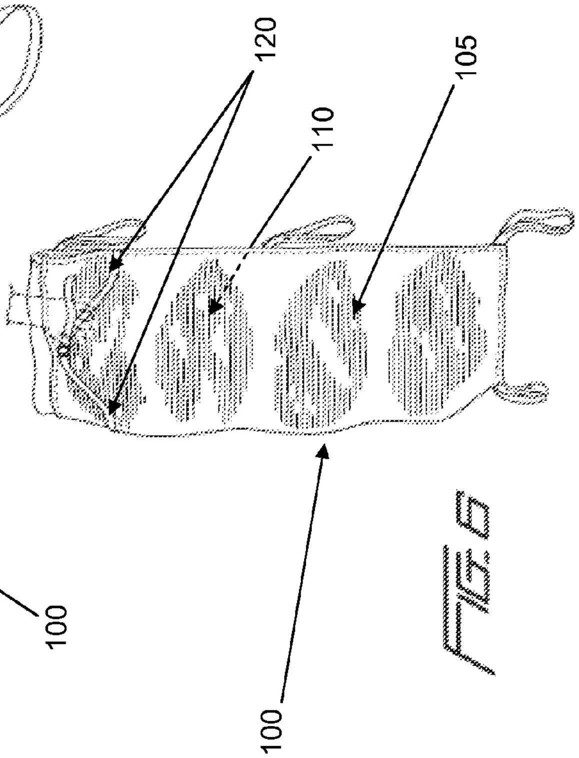
FIG. 6 illustrates an exemplarily embodiment of the collapsible litter apparatus employed as a duffel bag.

FIG. 6 shows the litter 100 in the duffle bag configuration. The first elongated body support member 110 and the second flexible support member 105 form the outer surfaces of the duffel bag. The extended portion of the elongated body support member 110 is used as a flap and is folded over the opening of the duffel bag to further secure and shield the bag contents. The body strap assembly 120 is disposed proximate to the opening formed by the unsecured edge of said second flexible body support member 105 and is used to cinch the opening and secure the duffel bag's compartment 155 when the litter assembly 110 is used as a duffel bag. The body strap assembly 120 is also used as the carry strap for the duffel bag as shown in FIG. 6. The flexible grab straps provide auxiliary handles and can be used to grab, maneuver or load the duffel bag when filled with heavy equipment.

In yet another embodiment the invention resides in a system for casualty evacuation including a compact collapsible litter 100 having a first flexible and elongated body support member 110 having a top and a bottom surface.

Figure 4:
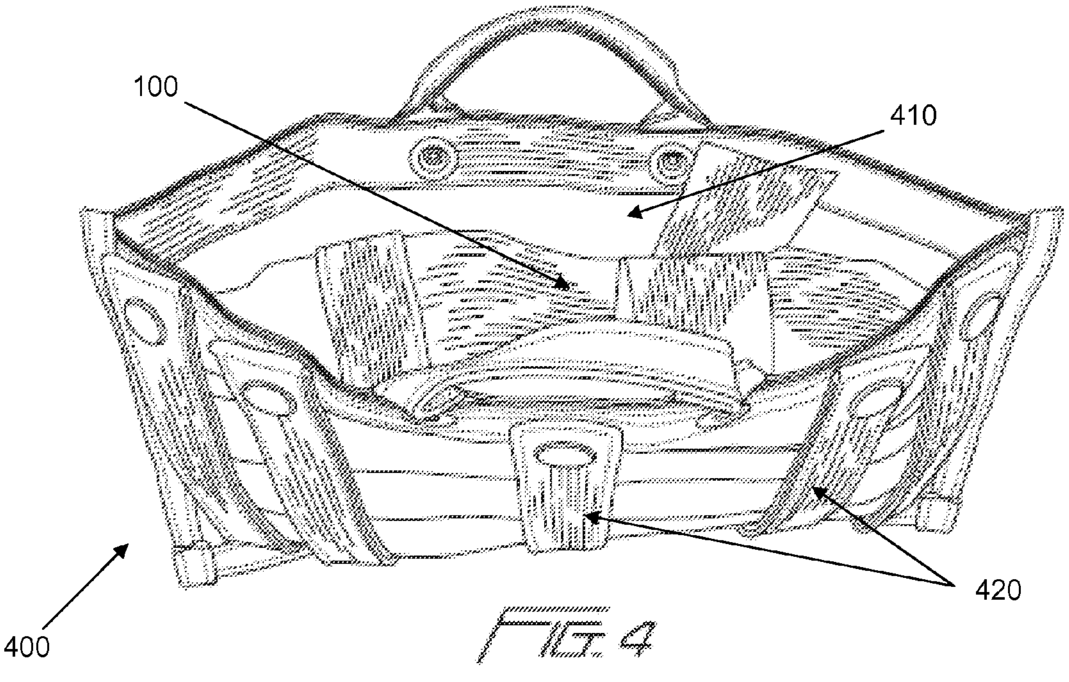
FIG. 4 illustrates an exemplarily embodiment of the collapsible litter apparatus folded for storage and stowed in an equipment pouch for incorporation into a MOLLE system.

Referring now to FIG. 4, with continued reference to FIGS. 1-3, the litter 100 features a plurality of flexible grab strap elements 115 attached to the bottom surface of the body support member extending substantially beyond the surface of the body support member 110. The litter includes a second flexible body support member 105 disposed on said top of the first flexible elongated body support member 110, at least three edges of the second flexible body support member 105 being rigidly affixed the top surface of said first flexible body support member 110.

The litter also includes at least one flexible body strap element 120 attached to and extending across the bottom surface of the first flexible elongated body support member 110. Each end of the body strap 120 extends substantially beyond the body support member 110 and includes an attachment means 125 disposed thereon.

The first and second body support members 105, 110 form a compartment 155 for securing and transporting equipment. The system also includes a storage device 400 for the compact collapsible litter 100. The storage device 400 features a sealable compartment 410 for housing the litter 100, and an attachment apparatus 420 for attaching and integrating the storage device 400 to existing equipment carried by a potential casualty or care giver.

Although specific example embodiments have been illustrated and described herein, those of ordinary skill in the art appreciate that other variations, aspects, or embodiments may be contemplated, and/or practiced without departing from the scope or the spirit of the appended claims.

We claim and seek letter of patent on:

1. A collapsible litter comprising:

a first flexible and elongated body support member having a top surface and a bottom surface;

a plurality of flexible grab strap elements attached to a surface of said first body support member, said strap elements extending substantially beyond the surface of said first body support member;

a second flexible body support member, said second body support member being disposed on said top of said first flexible elongated body support member overlaying about ⅔ of said first flexible elongated body support, said second flexible body support member having an upper edge region, a lower edge region and first and second side edge regions, said second flexible body support member being affixed to the top surface of said first elongated body support member proximate to at least three edges of said first elongated body support member; and at least one flexible body strap element attached to a surface of said first flexible elongated body support member, an end of said body strap extending substantially beyond said first flexible elongated body support member and having an attachment means disposed thereon, said at least one flexible body strap element being disposed proximate to the opening of said compartment.

2. The collapsible litter of claim 1 wherein said flexible body strap element disposed proximate to the opening of said compartment has an attachment thereon to facilitate closure of said compartment when said litter is used to secure items.

3. The collapsible litter of claim 1 having a plurality of body strap elements disposed along at least one end of the first elongated body support member, each of said body strap elements having attachment means disposed thereon to secure a casualty placed on the litter.

4. The collapsible litter of claim 1 wherein at least one of said body support members is constructed of a flexible ballistic material.

* * * * *